(12) United States Patent
Reznikoff et al.

(10) Patent No.: US 7,083,980 B2
(45) Date of Patent: Aug. 1, 2006

(54) TN5 TRANSPOSASE MUTANTS AND THE USE THEREOF

(75) Inventors: William S. Reznikoff, Madison, WI (US); Mindy M. Steiniger-White, Madison, WI (US); Jeremy D. Metzler, New Franken, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 8 days.

(21) Appl. No.: 10/826,573

(22) Filed: Apr. 16, 2004

(65) Prior Publication Data

US 2004/0235103 A1 Nov. 25, 2004

Related U.S. Application Data

(60) Provisional application No. 60/463,470, filed on Apr. 17, 2003.

(51) Int. Cl.
  *C12N 15/63* (2006.01)
  *C12N 15/85* (2006.01)
  *C12N 15/87* (2006.01)
  *C07K 1/00* (2006.01)
  *C07K 14/00* (2006.01)

(52) U.S. Cl. .................. 435/455; 435/461; 435/462; 530/350

(58) Field of Classification Search ............... 435/455, 435/461, 462
See application file for complete search history.

(56) References Cited

U.S. PATENT DOCUMENTS

| | | | |
|---|---|---|---|
| 4,980,290 | A | 12/1990 | Reznikoff et al. |
| 5,925,545 | A | 7/1999 | Reznikoff et al. |
| 5,948,622 | A | 9/1999 | Reznikoff et al. |
| 5,965,443 | A | 10/1999 | Reznikoff et al. |
| 6,159,736 | A | 12/2000 | Reznikoff et al. |
| 6,294,385 | B1 | 9/2001 | Goryshin et al. |
| 6,406,896 | B1 | 6/2002 | Reznikoff et al. |
| 6,437,109 | B1 | 8/2002 | Reznikoff et al. |

FOREIGN PATENT DOCUMENTS

WO  WO 98/10077  3/1998

OTHER PUBLICATIONS

Ahmed, Asad, "Use of Transposon-promoted Deletions in DNA Sequence Analysis," J. Mol. Biol. 178:941-948 (1984).
Ahmed, A., et al., "The revised nucleotide sequence of Tn5," Gene 154:129-130 (1995).
Benjamin, H.W., et al., "Excision of Tn10 from the donor site during transposition occurs by flush double-strand cleavages . . . ," Proc. natl. Acad. Sci. USA 89:4648-4652 (1992).
Bhasin, A., et al., "Characterization of a Tn5 Pre-cleavage Synaptic Complex," J. Mol. Biol. 302:49-63 (2000).
DeLong, A., et al, "Trans-acting transposase mutant from Tn5" Proc. Natl. Acad. Sci. USA 88:6072-6076 (1991).
Devine, S.E., et al., "Efficient integration of artificial transposons into plasmid targets in vitro: a useful tool for DNA mapping . . . ," Nucleic Acids Research 22:3765-3772 (1994).
Dower, W.J., et al., "High efficiency transformation of *E. coli* by high voltage electroporation," Nculeic Acids Research 16:6127-6145 (1988).
Goryshin, I.Y., et al., "Tn5 in Vitro Transposition," Teh Journal of Biological Chemistry, 273:7367-7374 (1998).
Goryshin, I.Y., et al., "Insertional transposon mutagenesis by electroporation of released Tn5 transposition complexes," Natur Biotechnology 18:97-100 (2000).
Hattori, M., et al., "A novel method for making nested deletions and its application for sequencing of a 300 kb region . . . ," Nucleic Acids Research 25:1802-1808 (1997).
Henikoff, S., "Unidirectional digestion with exonuclease III creates targeted breakpoints for DNA sequencing," Gene 28:351-359 (1984).

(Continued)

*Primary Examiner*—James Ketter
*Assistant Examiner*—Konstantina Katcheves
(74) *Attorney, Agent, or Firm*—Quarles & Brady LLP

(57) ABSTRACT

Tn5 transposase (Tnp) mutants that have higher transposase activities than the wild-type Tnp are disclosed. The Tn5 Tnp mutants differ from the wild-type Tnp at amino acid positions 54, 242, and 372 and have greater avidity than the wild-type Tnp for at least one of a wild-type Tn5 outside end sequence as defined by SEQ ID NO:3 and a modified Tn5 outside end sequence as defined by SEQ ID NO:5. Also disclosed are various systems and methods of using the Tnp mutants for in vitro or in vivo transposition.

20 Claims, 1 Drawing Sheet

OTHER PUBLICATIONS

Jilk, R.A., et al., "Implications of Tn5-Assocaited Adjacent Deletions," Journal of Bacteriology 175:1264-1271 (1993).

Johnson, R.C., et al., "DNA sequences at the ends of transposon Tn5 required for transposition," Nature 304:280-282 (1983).

Junop, M.S., et al., "Multiple roles for divalent metal ions in DNA transposition: distinct stages of Tn10 transposition have different Mg2+ requirements," The EMBO Journal 15:2547-2555 (1996).

Krebs, M.P., et al., "Use of a Tn5 derivative that creates lacZ translational fusions to obtain a transposition mutant," Gene 277-285 (1988).

Krishnan, B.R., et al., "Construction of a genomic DNA 'feature map' by sequencing from nested deletions: application to the HLA class 1 region," Nucleic Acids Research 23:117-122 (1995).

Kuspa, A., et al., "Tagging developmental genes in *Dictyostelium* by restriction enzyme-mediated integration of plasmid DNA," Proc. Natl. Acad. Sci. USA 89:8803-8807 (1992).

Leschziner, A.E., et al., "Tn552 transposase catalyzes concerted strand transfer in vitro," Proc. Natl. Acad. Sci. USA 95:7345-7350 (1998).

Lu et al., "Characterization of the Interaction Between the Tn7 Transposase (TnsA+B) and the Transposase Regulator TnsC," Keystone Symposia: Transposition and Site-Specific Recombination, Santa Fe (1997).

Mizuuchi, M., etal., "Assembly of the Active Form of the Transposase-Mu DNA Complex: A Critical Control Point in Mu Transposition," Cell 70:303-311 (1992).

Morgan, G., et al., Bacteriophage Mu Genome Spequence: Analysis and Comparison with Mu-like Prophages in *Haemophilus, Neisseria* and *Deinococcus*, GenBank AF 083977 (version AF 0839771.1 G1:6010378).

Morita, M., et al., "Nested Deletions from a Fixed Site as an Aid to Nucleotide Sequencing: an invitro System Using Tn3 Transposase," DNA Research 3:431-433 (1996).

Park, B.T., et al., "In Vitro Transpositin of Tn5," J. Korean Soc. Microbiol. 27:381-389 (1992).

Pues, H., et al., "Construction of a deletion library using a mixture of 5'-truncated primers for inverse PCR (IPCR)," Nucleic Acids Research 25:1303-1304 (1997).

Steiniger-White, M., et al., "The C-terminal alpha Helix of Tn5 Transposase is Required for Synaptic Complex Formation," The Journal of Biological Chemistry 275:23127-23133 (2000).

Tomcsanyi, T., et al., "Intramolecular Transposition by a Synthetic IS50 (Tn5) Derivative," Journal of Bacteriology 172:6348-6354 (1990).

Wang, G., et al., "pDUAL: A transposon-based cosmid cloning vector for generating nested deletions and DNA sequencing templates in vivo," Proc. natl. Acad. Sci. USA 90:7874-7878 (1993).

Wang, G., et al., "Inversions and Deletions Generated by a Mini-gamma delta (Nt1000) Transposon," Journal of Bacteriology 176:1332-1338 (1994).

Weinert, T.A., et al., "Replicative and Conservative Transpositional Recombination of Insertion Sequences," Cold Spring Harbor Symp. Quant. Biol. 49:251-260 (1984).

Weinreich, M.D., et al., "A Functional Analysis of the Tn5 Transposase Identification of Domains Required for DNA Binding and Multimerization," J. Mol. Biol. 241-166-177 (1993).

Weinreich, M.D., et al., "Evidence that the cis preference of the Tn5 transposase is caused by nonproductive multimerization," Genes & Development 8:2363-2374 (1994).

Wiegand, T.W., et al., "Characterization of Two Hypertransposing Tn5 Mutants," Journal of Bacteriology 174:1229-1239 (1992).

Weigand, T.W., et al., "Transposase mutants that increase the transposition frequency of Tn5," PhD Thesis (Abstract) University of Wisconsin-Madison (1993).

Yin, J.C., et al., "Effect of dam Methylation on Tn5 Transposition," J. ol. Biol. 199:35-45 (1988).

Yohda, M., et al., "Solid-Phase Nested Deletion: A New Subcloning-less Method for Generating Nestd Deletions," DNA Research 2:175-181 (1995).

York, D., et al., "Purification and biochemical analyses of a monomeric form of Tn5 transposase," Nucleic Acids Research 24:3790-3796 (1996).

York, D., et al., "DNA binding and phasing analyses of Tn5 transposase and a monomeric variant," Nucleic Acids Research 25:2153-2160 (1997).

Zhou, M., et al., "Three Types of Novel Mutations in the NH-2-Terminus of Tn5 Transposase: Structure/Function of Transposase," Keystone Symposium on Transposition and site-Specific Recombination: Mechanism adn Biology (Abstract) Jan. 1994 J. of Cell Biochem. Suppl. 0(18B).

Zhou, M., et al., "Tn5 Transposase Mutants that Alter DNA Binding Specificity," J. Mol. Biol. 271-362-373 (1997).

Zhu, K.Y., et al., "Rapid Construction of Nested Deletions of Recombinant Plasmid DNA for Dideoxy Sequencing," TioTechniques 18:222-224 (1995).

I.Y. Goryshin, et al., "DNA Length, Bending, and Twisting Constraints on IS50 Transposition," Proc. Natl. Acad. Sci. USA 91:10834-10838, 1994.

R.A. Jilk, et al., "The Organization of the Outside End of Transposon Tn5," J. Bacteriol. 178(6):1671-1679, 1996.

C. Sasakawa, et al., "Sequences Essential for Transposition at the Termini of IS50," Proc. Natl. Acad. Sci. USA 80:7293-7297, 1983.

US 7,083,980 B2

TN5 TRANSPOSASE MUTANTS AND THE USE THEREOF

CROSS-REFERENCE TO RELATED APPLICATIONS

This application claims the benefit of U.S. provisional patent application Ser. No. 60/463,470, filed on Apr. 17, 2003, incorporated by reference in its entirety.

STATEMENT REGARDING FEDERALLY SPONSORED RESEARCH OR DEVELOPMENT

This invention was made with United States government support awarded by the following agency: NIH, Grant No. GM50692 and USDA, Grant No. 02-CRHF-0-6055. The United States government has certain rights in this invention.

BACKGROUND OF THE INVENTION

Bacterial transposons such as Tn5 evolved within the cell by maintaining a low mobility level. While necessary for the transposon to survive, the low mobility level has inhibited the ability of researchers to detail the molecular transposition process and to exploit the transposition process for use, e.g., in the development of new diagnostic and therapeutic resources. Tn5 is a conservative "cut and paste" transposon of the IS4 family (Rezsohazy, R., Hallet, B., Delcour, J., and Mahillon, J., "The IS4 family of insertion sequences: evidence for a conserved transposase motif," *Mol Microbiol.* 9:1283–1295 (1993)) that encodes a 53 kD transposase protein (Tnp) that is responsible for its movement. The wild-type Tn5 transposase (Tnp) amino acid and nucleic acid sequences are known (Ahmed, A. and Podemski, L. The Revised Sequence of Tn5. Gene 154(1),129–130(1995), incorporated by reference as if set forth herein in its entirety). A nucleic acid sequence that encodes wild-type Tn5 Tnp is attached as SEQ ID NO:1. A polypeptide sequence encoded by SEQ ID NO:1 which corresponds to wild-type Tn5 Tnp is attached as SEQ ID NO:2.

The Tnp protein facilitates movement of the entire element by binding initially to each of two 19 bp specific binding sequences termed outside end (OE; SEQ ID NO:3), followed by formation of a nucleoprotein structure termed a synapse, blunt ended cleavage of each end, association with a target DNA, and then strand transfer (Reznikoff, W. S., Bhasin, A., Davies, D. R., Goryshin, I. Y., Mahnke, L. A., Naumann, T., Rayment, I., Steiniger-White, M., and Twining, S. S., "Tn5: A molecular window on transposition," *Biochem. Biophys. Res. Commun.* 266:729–34 (1999)). Tn5 Tnp can also promote movement of a single insertion sequence by using a combination of OE and inside end (IE; SEQ ID NO:4) sequences. The IE is also 19 bp long and is identical to OE at 12 of 19 positions. In vivo, Tn5 Tnp exhibits a marked preference for OE in *E. coli*. Transposase recognition and binding to IE is inhibited in *E. coli* by the presence of four dam methylation sites (GATC palindromes) which add four methyl groups per inside end sequence ($IE^{ME}$; also depicted as SEQ ID NO:4, methylation not shown) (Yin, J. C. P., Krebs, M. P., and Reznikoff, W. S., "Effect of dam Methylation on Tn5 Transposition," *J. Mol Biol.*, 199:35–45 (1988), incorporated by reference as if set forth herein in its entirety). This methylation reduces tranhsposition by reducing protein-DNA primary recognition (Jilk, R. A., York, D., and Reznikoff, W. S., "The organization of the outside end of transposon Tn5, " *J. Bacteriol.* 178:1671–1679 (1996)).

Tn5 transposon also encodes an inhibitor protein that can interfere with transposase activity. The inhibitor-encoding sequence overlaps with the sequence that encodes the transposase. An AUG in the wild-type Tn5 Tnp gene that encodes methionine at transposase amino acid 56 is the first codon of the inhibitor protein. Replacement of the methionine at position 56 with an alanine has no apparent effect upon the transposase activity. However, it prevents translation of the inhibitor protein and thus results in a higher transposition rate. Weigand, T. W. and W. S. Reznikoff, "Characterization of Two Hypertransposing Tn5 Mutants," J. Bact. 174:1229–1239 (1992), incorporated herein by reference.

A principal roadblock to understanding how Tn5 Tnp works is the fact that purified wild-type Tnp has no detectable activity in vitro. Recently, a double mutant hyperactive form of transposase ("Tnp EK/LP") that promotes the transposition reaction in vitro was developed (U.S. Pat. No. 5,965,443, incorporated herein by reference in its entirety). The Tnp EK/LP protein differs from wild-type Tn5 Tnp at position 54 (Glu to Lys mutation) and at position 372 (Leu to Pro mutation), in addition to a non-essential but advantageous change at position 56 that prevents production of the inhibitor protein. The modified hyperactive Tnp protein increases the dramatic preference for OE termini of wild-type Tn5 Tnp. In addition, certain modifications on the OE sequence have been shown to increase the transposition frequency by Tnp EK/LP (U.S. Pat. No. 5,925,545 and U.S. Pat. No. 6,437,109, both of which are herein incorporated by reference in their entirety). Tnp EK/LP has clarified many aspects of Tn5 transposition that were not previously adequately addressable in vivo.

Another recent development in Tn5 research involves the identification of Tn5 mutants that have a higher avidity for IE than OE sequences (U.S. Pat. No. 6,406,896, which is herein incorporated by reference in its entirety). These mutants contain a mutation at amino acid position 58 and can further contain a mutation at amino acid position 8, 344, or both. Both unmethylated and methylated IE ($IE^{ME}$) sequences can be used efficiently for transposition by these Tn5 mutants.

In vitro polynucleotide transposition is a powerful tool for introducing random or targeted mutations into a genome. Useful in vitro transposition systems based upon the Tn5 transposon are disclosed in U.S. Pat. No.5,948,622, 6,159, 736 and U.S. Pat. No. 6,406,896, all of which are incorporated herein by reference in their entirety.

BRIEF SUMMARY OF THE INVENTION

The present invention is summarized in that Tn5 Tnp mutants modified relative to the wild-type enzyme at amino acid positions 54, 242, and 372 have higher transposase activities than the wild-type enzyme. These mutants have greater avidity than the wild-type Tnp for at least one of a wild-type Tn5 outside end sequence as defined by SEQ ID NO:3 and a modified Tn5 outside end sequence as defined by SEQ ID NO:5 and can be used in a variety of in vitro and in vivo transposition applications.

In one aspect, the present invention relates to a polypeptide or isolated polypeptide that contains a Tn5 Tnp mutant of the present invention.

In another aspect, the present invention relates to a nucleic acid or isolated nucleic acid that contains a polynucleotide encoding a Tn5 Tnp mutant of the present invention. Optionally, the nucleic acid can contain a transcription control sequence operably linked to the Tnp mutant-encoding polynucleotide. A host cell containing the above nucleic acid is also within the scope of the present invention.

In another aspect, the present invention relates to a method of using a polypeptide containing a Tn5 Tnp mutant of the present invention for inter- or intra-molecular transposition in vitro as described in U.S. Pat. No. 5,948,622.

In another aspect, the present invention relates to a method for forming a synaptic complex using a Tn5 Tnp mutant of the present invention and further introducing the complex into a target cell to make random or quasi-random insertional mutations in the cellular nucleic acid as described in U.S. Pat. No. 6,159,736.

The invention will be more fully understood upon consideration of the following detailed description taken in conjunction with the accompanying drawing.

DETAILED DESCRIPTION OF THE INVENTION

Figure 1:
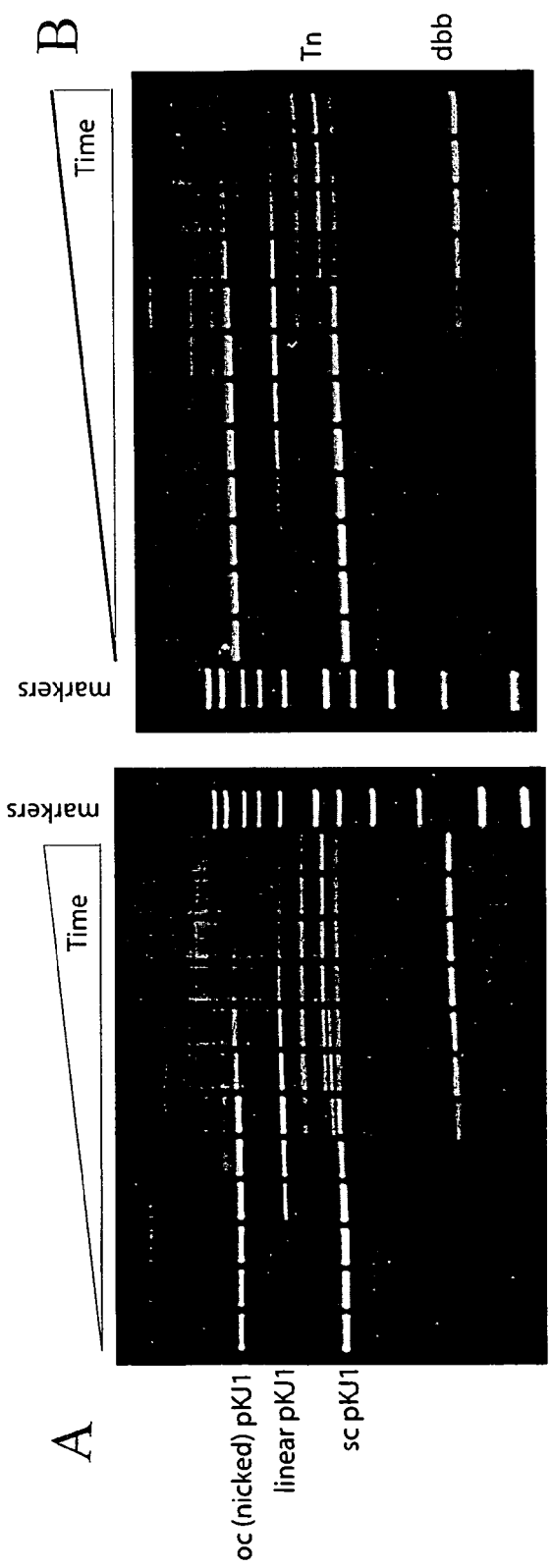
FIGS. 1A and 1B show agarose gel pictures of in vitro transposition reactions for Tn5 Tnp mutants EK54/LP372/PA242 and EK54/LP372, respectively, using pKJ1 as the substrate. All important substrate, intermediate, and product DNAs are labeled: sc=supercoiled, oc=open circle, Tn=transposon, dbb=donor backbone.
FIG. 1C shows a plot of the percentage of supercoiled substrate in each lane (determined by quatitation with Total Lab software) of FIGS. 1A and 1B versus time. The data were fit to a one-phase exponential decay equation to determine the observed rate. The error bars represent one standard deviation.
Figure 1:
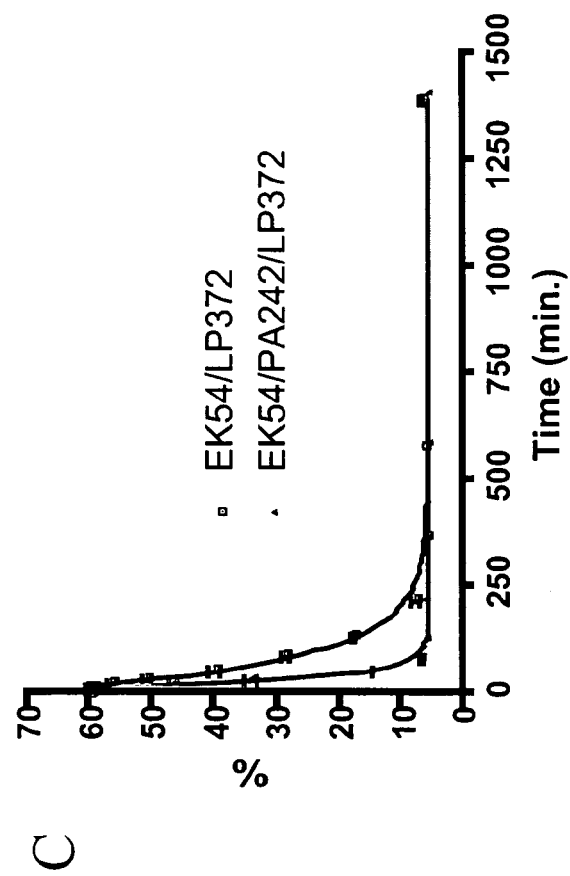

The term "polypeptide" and the term "protein" are used interchangeably in the specification and claims.

The term "isolated polypeptide" or "isolated nucleic acid" used in the specification and claims means a polypeptide or nucleic acid isolated from its natural environment or prepared using synthetic methods such as those known to one of ordinary skill in the art. Complete purification is not required in either case. Amino acid or nucleotide sequences that flank a polypeptide or nucleic acid in nature can but need not be absent from the isolated form. A polypeptide and nucleic acid of the invention can be isolated and purified from normally associated material in conventional ways such that in the purified preparation the polypeptide or nucleic acid is the predominant species in the preparation. At the very least, the degree of purification is such that the extraneous material in the preparation does not interfere with use of the polypeptide or nucleic acid of the invention in the manner disclosed herein. The polypeptide or nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than three separate genes. The term therefore covers, for example, (a) a DNA that has the sequence of part of a naturally occurring genomic DNA molecule but which is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library. An isolated nucleic acid molecule can be modified or unmodified DNA or RNA, whether fully or partially single-stranded or double-stranded or even triple-stranded. A modified nucleic acid molecule can be chemically or enzymatically induced and can include so-called non-standard bases such as inosine.

Tn5 Tnp mutants that differ from the wild-type enzyme at amino acid positions 54 and 372 (the 54/372 mutants) have previously been shown to possess higher than wild-type transposase activity, making these mutants suitable for in vitro transposition applications (U.S. Pat. No. 5,965,443 and U.S. Pat. No. 5,925,545). It is disclosed here that introducing another mutation to the 54/372 mutants at amino acid position 242 (the 54/242/372 mutants) will not abolish the higher-than-wild-type activity of the 54/372 mutants and in many cases will further increase the transposase activity of the 54/372 mutants. In addition, modifications on an OE sequence that are known to increase the transposition frequency of the 54/372 mutants (U.S. Pat. No. 5,925,545 and U.S. Pat. No. 6,437,109) can similarly increase the transposition frequency of the 54/242/372 mutants. Accordingly, a 54/242/372 mutant can be used similarly as a 54/372 mutant in various in vitro transposition applications as described in U.S. Pat. No. 5,925,545, U.S. Pat. No. 5,948, 622, and U.S. Pat. No. 6,159,736.

As shown in Example 2 provided below, when the modified OE sequence defined by SEQ ID NO:5 is employed for in vitro transposition, all eight 54/242/372 mutants constructed by the inventors as examples of the present invention displayed higher transposition activity than the 54/372 mutant. When wild-type OE sequence defined by SEQ ID NO:3 is employed, five out of eight 54/242/372 mutants displayed higher in vitro transposition activity than the 54/372 mutant. Although three of the eight 54/242/372 mutants catalyzed DNA transposition at a lower rate using the wild-type OE sequence than the 54/372 mutant, they nonetheless displayed in vitro transposition activity and thus can be used with the wild-type OE for in vitro transposition. A preferred way of practicing the present invention is to use a 54/242/372 mutant with an OE sequence that in combination provide a higher transposition activity than the 54/372 mutant and the OE sequence. Besides the combinations disclosed in Example 2 below, other "54/242/372 mutant-OE" combinations with transposition activity higher than the "54/372 mutant-OE" combination can be readily identified by a skilled artisan using the method in Example 2 or other methods with which the skilled artisan is familiar.

In one aspect, the present invention relates to a Tn5 Tnp mutant or isolated Tn5 Tnp mutant that contains a mutation at position 54, 242, and 372 in comparison to the wild-type Tn5 Tnp and has greater avidity than wild-type Tn5 Tnp for at least one of the Tn5 OE sequence defined by SEQ ID NO:3 and the modified Tn5 OE sequence defined by SEQ ID NO:5. Preferably, the mutations are substitution mutations. Examples of mutations on a Tn5 Tnp mutant include but are not limited to glutamic acid to lysine or valine at position 54, leucine to proline or glutamine at position 372, and proline to alanine, glycine, valine, leucine, isoleucine, tyrosine, phenylalanine, or aspartic acid at position 242.

Optionally, a Tn5 Tnp mutant of the present invention further contains a mutation at position 56 in comparison to the wild-type Tn5 Tnp. For example, the methionine at position 56 of the wild-type Tn5 Tnp can be substituted with alanine. Although such a mutation has no apparent effect upon the transposase activity, it prevents translation of a Tn5 Tnp inhibitor protein encoded in partially overlapping sequence with the transposase, leading to a higher transposition rate. Weigand, T. W. and W. S. Reznikoff, "Characterization of Two Hypertransposing Tn5 Mutants," *J. Bact.* 174:1229–1239 (1992), incorporated herein by reference. Thus, a preferred Tn5 Tnp mutant of the present invention includes an amino acid other than methionine at amino acid position 56 to ensure the absence of the inhibitor from the in vitro system of the present invention (described below). However, it should be noted a position 56 mutation is not essential to the present invention because other means can be used to eliminate the inhibitor from the in vitro system. For example, the inhibitor protein can be separated from the Tn5 Tnp according to differences in size between the two proteins.

It is appreciated that additional amino acid sequences can be added to the N-terminus, C-terminus or both of a Tn5 Tnp mutant of the present invention without reducing the transposase activity to the level of the wild-type enzyme. A polypeptide or isolated polypeptide containing the Tn5 Tnp mutant flanked by the additional amino acid sequences as described above is within the scope of the present invention. A flanking amino acid sequence can but does not have to assist in purification, detection, or stabilization of the Tn5 Tnp mutant.

In another aspect, the present invention relates to a nucleic acid or isolated nucleic acid that contains a polynucleotide encoding a Tn5 Tnp mutant of the present invention. The nucleic acid can further contain a native or non-native transcription control sequence (e.g., a promoter) operably linked to the Tn5 Tnp mutant-encoding polynucleotide. In addition, the present invention also encompasses a host cell that contains the nucleic acid of the present invention.

In another aspect, the present invention relates to a system for transposing a transposable DNA sequence in vitro. The system includes a polypeptide that contains a Tn5 Tnp mutant of the present invention, a donor DNA molecule containing the transposable DNA sequence that is flanked at its 5'- and 3'-ends by wild-type Tn5 OE sequences or modified Tn5 OE sequences that are active for in vitro transposition (defined below), and a target DNA molecule into which the transposable sequence can transpose.

In a related aspect, the present invention relates to a method of in vitro transposition using the transposition system described above. The method involves combining the donor DNA, the target DNA, and the Tn5 Tnp mutant-containing polypeptide in a suitable reaction buffer under suitable transposition conditions for a period of time sufficient for the transposase to catalyze the in vitro transposition. Details on suitable reaction buffers and reaction conditions are described in U.S. Pat. No. 5,925,545 and Goryshin, I. Y., and Reznikoff, W. S., "Tn5 in vitro transposition," *J. Biol. Chem.* 273:7367–7374 (1998), incorporated by reference as if set forth herein in its entirety. Although in U.S. Pat. No. 5,925,545 and Goryshin and Reznikoff (1998) the in vitro transposition was carried out with a two-step temperature incubation (below physiological temperature for binding of transposase to OE and physiological temperature for transposition), it is noted here that the whole procedure can also be carried out at a single temperature, the physiological temperature (e.g., 37° C.).

The donor DNA can be circular or linear. If the donor DNA is linear, the OE sequences flanking the transposable DNA sequence can be at the termini of the linear donor DNA or the donor DNA can include some nucleotides upstream and downstream from the OE sequences.

Either wild-type or modified OE sequences can be used for flanking a transposable DNA sequence in the donor DNA molecule. Examples of modified OE sequences that confer an in vitro transposition frequency at least as high as the wild-type sequence are described in U.S. Pat. No. 5,925,545. Other modified OE sequences not specifically described in U.S. Pat. No. 5,925,545 can also be used as long as the combination of a sequence and a Tn5 Tnp mutant of the present invention results in a detectable level of transposition in vitro. Such modified OE sequences are referred to as modified OE sequences that are active for in vitro transposition and can be readily identified by a skilled artisan using the screening method disclosed in U.S. Pat. No. 5,925,545.

The transposable DNA sequence between the OE sequences can include any desired nucleotide sequence. The length of the transposable DNA sequence between the OE sequences should be at least about 50 nucleotides, although smaller inserts may work. No upper limit to the insert size is known. However, it is known that a transposable DNA sequence of about 300 nucleotides in length can function well. By way of non-limiting examples, the transposable DNA sequence can include a coding region that encodes a detectable or selectable protein, with or without associated regulatory elements such as promoter, terminator, or the like.

If the transposable DNA sequence includes such a detectable or selectable coding region without a promoter, it will be possible to identify and map promoters in the target DNA that are uncovered by transposition of the coding region into a position downstream thereof, followed by analysis of the nucleic acid sequences upstream from the transposition site.

Likewise, the transposable DNA sequence can include a primer binding site that can be transposed into the target DNA, to facilitate sequencing methods or other methods that rely upon the use of primers distributed throughout the target genetic material. Similarly, the method can be used to introduce a desired restriction enzyme site or polylinker, or a site suitable for another type of recombination, such as a cre-lox, into the target.

The target DNA into which a transposable DNA sequence is transposed does not have any specific sequence requirements. Wild-type Tn5 Tnp has few, if any, preference for insertion sites. The Tn5 Tnp mutants disclosed here are believed to be the same. Accordingly, the method of the present invention can introduce changes into any target DNA.

In another aspect, the present invention relates to a method of using the Tn5 Tnp mutants disclosed herein for in vitro intra-molecular transpositions as described in U.S. Pat. No. 5,948,622. The molecule involved in this method is a genetic construct that contains a transposable portion and a donor backbone portion. The transposable portion contains an origin of replication, a nucleotide sequence of interest, and a pair of the wild-type or modified Tn5 OE sequences. The method involves combining, in an in vitro reaction mix, a polypeptide that contains the Tn5 Tnp mutant with the genetic construct described above at a low concentration, to generate reaction products, transforming the reaction products into a host cell, proliferating the host cell to obtain multiple transformed cells, and selecting from among the multiple transformed cells for cells that contain a DNA molecule that has lost the donor backbone portion and that contain a transposition of the nucleotide sequence of interest. By low concentration, we mean that the genetic construct's concentration is relatively low so that intramolecular transposition, as opposed to intermolecular transposition, is encouraged. A skilled artisan can readily determine the suitable low concentrations for a particular application. Generally speaking, the applicants have found a suitable amount of nucleic acid to be in the range of 0.05–0.005 µg/µl of reaction mix. At 0.05 µg/µl, 95% of the transposition events are intramolecular. At 0.005 µg/µl, or lower, about 100% of the events are intramolecular transpositions. Details on how to practice the method are described in U.S. Pat. No. 5,948,622.

In another aspect, the present invention relates to a method for forming a synaptic complex in vitro between a Tn5 Tnp mutant herein disclosed and a polynucleotide that contains a transposable nucleotide sequence flanked by a pair of the wild-type or modified OE sequences. The method involves combining the Tn5 Tnp mutant with the polynucleotide in vitro under conditions that disfavor polynucleotide strand transfer. The synaptic complex formed can be introduced into a target cell under suitable conditions to make an insertional mutation at a random or quasi-random position in the cellular nucleic acid. By making an insertional mutation at a quasi-random position, we mean that the insertion event has a slight preference for one sequence over another. Details on how to form the synaptic complex and how to introduce the complex into a cell to make insertonal mutations are described in U.S. Pat. No. 6,159,736.

The present invention will be more readily understood upon consideration of the following examples which are exemplary and are not intended to limit the scope of the invention.

EXAMPLE 1

In Vivo Transposition with Tn5 Tnp Mutants

EK54/LP372/PA242 Tnp (proline to alanine mutation at position 242) and EK54/LP372/PG242 Tnp (proline to glycine mutation at position 242) were constructed by overlap PCR. Bases corresponding to aa 141-358 were amplified from pRZ10300 (Steiniger-White, M., and Reznikoff, W. S. "The C-terminal alpha helix of Tn5 transposase is required for synaptic complex formation," *J. Biol. Chem.* 275: 23127–33 (2000), incorporated by reference in its entirety) using Pfu polymerase and internal mismatched primers containing the mutation. The external primers included Tnp NheI and NotI sites. PCR products were digested with NheI (New England Biolabs, Beverly, Mass.) and NotI (Promega, Madison, Wis.) and ligated to the large NotI-NheI fragment of both pRZPET2 (Goryshin and Reznikoff, 1998) and pGRTYB35 (Bhasin, A., Goryshin, I. Y., Steiniger-White, M., York, D., and Reznikoff, W. S. "Characterization of a Tn5 pre-cleavage synaptic complex," *J. Mol. Biol.* 302: 49–63 (2000), incorporated by reference in its entirety). Each mutant Tnp was purified from its pGRTYB35 construct as described previously (Bhasin et al., 1999). Because all mutations were created in an EK54/LP372 background, mutant Tnps will be defined by their additional mutations.

Mutations constructed in pRZPET2 were tested for in vivo activity using a papillation assay (Steiniger-White and Reznikoff, 2000). In this assay, the movement of a transposon having a promoterless lacZ gene flanked by OEs from its original plasmid to the chromosome is assessed. When the transposon inserts into the chromosome in the correct reading frame and orientation downstream from an active promoter and translation initiation signals, the lacZ gene is transcribed. Cells producing β-galactosidase have a growth advantage because they can utilize phenyl-β-D-galactoside provided in the media, while cells not producing β-galactosidase stop growing once all glucose is metabolized. Because cells producing β-galactosidase continue to grow, they will appear raised above the rest of the colony. These cells are made visible by including X-gal in the media. This assay allows qualitative assessment of in vivo transposition activity and showed that both EK54/LP372/PA242 Tnp and EK54/LP372/PG242 Tnp were hyperactive compared to EK54/LP372 Tnp.

EXAMPLE 2

In Vitro Transposition with Tn5 Tnp Mutants

Eight Tn5 Tnp mutants were constructed by the method described in Example 1: EK54/LP372/PA242, EK54/LP372/PG242, EK54/LP372/PV242, EK54/LP372/PL242, EK54/LP372/PI242, EK54/LP372/PY242, EK54/LP372/PF242, and EK54/LP372/PD242. These mutants and EK54/LP372 Tnp were tested for in vitro transposition using two different substrates, pKJ1 and pKJ4. pKJ1 is a pUC19 vector with a 1,200 bp transposon (Tn) flanked by wild-type OEs (SEQ ID NO:3) while pKJ4 is isogenic to pKJ1 except that the Tn is flanked by modified OE sequence as defined by SEQ ID NO:5.

The in vitro transposition assay was performed as follows. 12 nM plasmid substrate (pKJ1 or pKJ4) was incubated with either 100 nM (for pKJ4) or 250 nM (for pKJ1) Tnp mutant in 100 mM potassium glutamate, 20 mM HEPES, pH 7.5, and 10 mM magnesium acetate at 37° C. 10 µL timepoints were taken at various intervals and added to 5 µL 1% SDS to stop the reaction. 5 µL of agarose gel loading dye were added following completion of all time points and 6 µL of each timepoint were run on a 1.3% agarose gel to separate reaction products. All reactions were performed in triplicate.

To determine the rate of decrease in substrate utilization for each Tnp mutant, the reaction products in each lane were quantitated using Total Lab software (Image Quant). The percentage of total DNA in each lane that corresponded to supercoiled substrate was then plotted versus time. These data were then fit to a one-phase exponential decay equation $Y=\text{If}(X<X0, \text{Plateau}, \text{Bottom} +(\text{Plateau}-\text{Bottom})*\exp(-k*(X-X0)))$; where k is observed rate constant for the decrease in supercoiled substrate. Transposase activity was assessed as the rate of decrease in supercoiled substrate over time ($k_{obs}$ ($\sec^{-1}$)).

As examples, the agarose gel pictures for mutants EK54/LP372/PA242 and EK54/LP372 are shown in FIG. 1A and FIG. 1B, respectively. The one-phase exponential curves for these two mutants are shown in FIG. 1C. The in vitro transposase activity (expressed as the rate of decrease in supercoiled substrate) of all the Tn5 Tnp mutants tested is summarized in Table 1. As shown in Table 1, all Tn5 Tnp mutants of the present invention tested had detectable in vitro transposition activity. When modified OE sequence defined by SEQ ID NO:5 (pKJ4) was employed for transposition, all eight Tn5 Tnp mutants of the present invention tested had higher activity than the EK54/LP372 mutant. When the wild-type OE sequence defined by SEQ ID NO:3 (pKJ1) was employed, five out of eight Tn5 Tnp mutants of the present invention tested had higher activity than the EK54/LP372 mutant.

TABLE 1

The observed rate constants for all Tn5 Tnp mutants tested on pKJ1 and pKJ4. Standard deviations are listed in parentheses.

| Tnp mutant | $K_{obs}$ (sec$^{-1}$) for decrease in supercoiled substrate | |
|---|---|---|
| | pKJ4 (with 100 nM Tnp) | pKJ1 (with 250 nM Tnp) |
| EK54/LP372 | 1.45 (0.08) | 0.79 (0.03) |
| EK54/LP372/PA242 | 2.60 (0.09) | 2.52 (0.14) |
| EK54/LP372/PG242 | 2.22 (0.08) | 2.50 (0.10) |
| EK54/LP372/PV242 | 2.80 (0.13) | 1.42 (0.06) |
| EK54/LP372/PL242 | 2.89 (0.19) | 1.56 (0.07) |
| EK54/LP372/PI242 | 3.01 (0.36) | 0.94 (0.03) |
| EK54/LP372/PY242 | 2.48 (0.13) | 0.60 (0.04) |
| EK54/LP372/PF242 | 1.90 (0.12) | 0.58 (0.03) |
| EK54/LP372/PD242 | 2.93 (0.18) | 0.55 (0.03) |

The foregoing examples are not intended to limit the scope of the invention. Rather the invention is understood to encompass all the variations and modifications that come within the scope of the appended claims.

We claim:

1. A polypeptide comprising a Tn5 transposase mutant modified relative to SEQ ID NO:2, the transposase mutant comprising a mutation at position 54 of SEQ ID NO:2, a mutation at position 242 of SEQ ID NO:2, and a mutation at position 372 of SEQ ID NO:2, wherein the transposase mutant has greater avidity than wild-type Tn5 transposase for at least one of a Tn5 outside end sequence as defined by SEQ ID NO:3 and a modified Tn5 outside end sequence as defined by SEQ ID NO:5.

2. A polypeptide as claimed in claim 1 wherein the mutation at position 54 of the Tn5 transposase mutant is a substitution mutation.

3. A polypeptide as claimed in claim 2 wherein position 54 of the Tn5 transposase mutant is a lysine.

4. A polypeptide as claimed in claim 2 wherein position 54 of the Tn5 transposase mutant is a valine.

5. A polypeptide as claimed in claim 1 wherein the mutation at position 372 of the Tn5 transposase mutant is a substitution mutation.

6. A polypeptide as claimed in claim 5 wherein position 372 of the Tn5 transposase mutant is a proline.

7. A polypeptide as claimed in claim 5 wherein position 372 of the Tn5 transposase mutant is a glutamine.

8. A polypeptide as claimed in claim 1 wherein the mutation at position 242 of the Tn5 transposase mutant is a substitution mutation.

9. A polypeptide as claimed in claim 8 wherein position 242 of the Tn5 transposase mutant is an amino acid selected from the group consisting of alanine, glycine, valine, leucine, isoleucine, tyrosine, phenylalanine, and aspartic acid.

10. A polypeptide as claimed in claim 1 wherein the Tn5 transposase mutant further comprises a substitution mutation at position 56 of SEQ ID NO:2, wherein the transposase mutant lacks an inhibitor activity.

11. A polypeptide as claimed in claim 10 wherein position 56 of the Tn5 transposase mutant is an alanine.

12. A Tn5 transposase mutant modified relative to SEQ ID NO:2, the transposase mutant comprising a mutation at position 54 of SEQ ID NO:2, a mutation at position 242 of SEQ ID NO:2, and a mutation at position 372 of SEQ ID NO:2, wherein the transposase mutant has greater avidity than wild-type Tn5 transposase for at least one of a Tn5 outside end sequence as defined by SEQ ID NO:3 and a modified Tn5 outside end sequence as defined by SEQ ID NO:5.

13. A nucleic acid comprising a polynucleotide that encodes the Tn5 transposase mutant as claimed in claim 12.

14. A nucleic acid as claimed in claim 13 further comprising a transcriptional control sequence operably linked to the polynucleotide that encodes the Tn5 transposase mutant.

15. A host cell comprising a nucleic acid as claimed in claim 13.

16. A system for transposing a transposable DNA sequence in vitro, the system comprising:
the polypeptide of claim 1;
a donor DNA molecule comprising the transposable DNA sequence, the transposable DNA sequence being flanked at its 5'- and 3'-ends by sequences selected from the group consisting of a wild-type Tn5 outside end sequence and a modified Tn5 outside end sequence that is active for in vitro transposition; and
a target DNA molecule into which the transposable DNA sequence can transpose.

17. A method for in vitro transposition, the method comprising the steps of:
combining a donor DNA molecule that comprises a transposable DNA sequence of interest with a target DNA molecule and the polypeptide of claim 1 in a suitable reaction buffer for a period of time sufficient for the enzyme to catalyze in vitro transposition,
wherein the transposable DNA sequence of interest is flanked at its 5'- and 3'-ends by a pair of sequences selected from the group consisting of a wild-type Tn5 outside end sequence and modified Tn5 outside end sequences that are active for in vitro transposition.

18. A method for in vitro transposition in a genetic construct that comprises a transposable portion and a donor backbone portion, the transposable portion comprising an origin of replication, a nucleotide sequence of interest, and a pair of sequences flanking the donor backbone portion, the pair of sequences being selected from the group consisting of a wild-type Tn5 outside end sequence and modified Tn5 outside end sequences that are active for in vitro transposition, the method comprising the steps of:
combining, in an in vitro reaction mix, the polypeptide of claim 1 and the genetic construct at a concentration suitable for generating intramolecular transposition, to generate reaction products;
transforming the reaction products into a host cell;
proliferating the host cell to generate multiple transformed cells; and
selecting from among the multiple transformed cells for cells that comprise (i) a DNA molecule that has lost the donor backbone portion and (ii) a transposition of the nucleotide sequence of interest.

19. A method for forming a synaptic complex between (a) the polypeptide of claim 1 and (b) a polynucleotide that comprises a pair of sequences and a transposable nucleotide sequence therebetween, wherein the pair of sequences are selected from the group consisting of a wild-type Tn 5 outside end sequence and modified Tn5 outside end sequences that are active for in vitro transposition, the method comprising the step of:
combining (a) and (b) in vitro under conditions that disfavor polynucleotide strand transfer to form the synaptic complex.

20. A method for making an insertional mutation in cellular nucleic acid in a target cell, the method comprising the step of:
introducing into the target cell a synaptic complex according to claim 19 under conditions that mediate transpositions into the cellular nucleic acid.

* * * * *

UNITED STATES PATENT AND TRADEMARK OFFICE
CERTIFICATE OF CORRECTION

PATENT NO. : 7,083,980 B2 Page 1 of 1
APPLICATION NO. : 10/826573
DATED : August 1, 2006
INVENTOR(S) : William S. Reznikoff et al.

It is certified that error appears in the above-identified patent and that said Letters Patent is hereby corrected as shown below:

Column 1, Lines 63-64: "tranhsposition" should be -- transposition --.

Column 2, Line 30: "TnS" should be -- Tn5 --.

Signed and Sealed this

Sixteenth Day of January, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,083,980 B2 | Page 1 of 1 |
| APPLICATION NO. | : 10/826573 | |
| DATED | : August 1, 2006 | |
| INVENTOR(S) | : William S. Reznikoff et al. | |

It is certified that error appears in the above-identified patent and that said Letters Patent is hereby corrected as shown below:

In the Specification

Column 1, Lines 13-17:
Delete the phrase:
"This invention was made with United States government support awarded by the following agency: NIH, Grant No. GM50692 and USDA, Grant No. 02-CRHF-0-6055. The United States government has certain rights in this invention."

And replace with:
--This invention was made with government support under 02-CRHF-0-6055 awarded by the USDA/NIFA and GM050692 awarded by the National Institutes of Health. The government has certain rights in the invention.--.

Signed and Sealed this
First Day of December, 2020

Andrei Iancu
*Director of the United States Patent and Trademark Office*

SEQUENCE LISTING

<160> NUMBER OF SEQ ID NOS: 5

<210> SEQ ID NO 1
<211> LENGTH: 1431
<212> TYPE: DNA
<213> ORGANISM: Transposon Tn5
<220> FEATURE:
<221> NAME/KEY: CDS
<222> LOCATION: (1)..(1428)

<400> SEQUENCE: 1

```
atg ata act tct gct ctt cat cgt gcg gcc gac tgg gct aaa tct gtg      48
Met Ile Thr Ser Ala Leu His Arg Ala Ala Asp Trp Ala Lys Ser Val
1               5                   10                  15 ttc tct tcg gcg gcg ctg ggt gat cct cgc cgt act gcc cgc ttg gtt      96
Phe Ser Ser Ala Ala Leu Gly Asp Pro Arg Arg Thr Ala Arg Leu Val
            20                  25                  30 aac gtc gcc gcc caa ttg gca aaa tat tct ggt aaa tca ata acc atc     144
Asn Val Ala Ala Gln Leu Ala Lys Tyr Ser Gly Lys Ser Ile Thr Ile
        35                  40                  45 tca tca gag ggt agt gaa gcc atg cag gaa ggc gct tac cga ttt atc     192
Ser Ser Glu Gly Ser Glu Ala Met Gln Glu Gly Ala Tyr Arg Phe Ile
    50                  55                  60 cgc aat ccc aac gtt tct gcc gag gcg atc aga aag gct ggc gcc atg     240
Arg Asn Pro Asn Val Ser Ala Glu Ala Ile Arg Lys Ala Gly Ala Met
65                  70                  75                  80 caa aca gtc aag ttg gct cag gag ttt ccc gaa ctg ctg gcc att gag     288
Gln Thr Val Lys Leu Ala Gln Glu Phe Pro Glu Leu Leu Ala Ile Glu
            85                  90                  95 gac acc acc tct ttg agt tat cgc cac cag gtc gcc gaa gag ctt ggc     336
Asp Thr Thr Ser Leu Ser Tyr Arg His Gln Val Ala Glu Glu Leu Gly
            100                 105                 110 aag ctg ggc tct att cag gat aaa tcc cgc gga tgg tgg gtt cac tcc     384
Lys Leu Gly Ser Ile Gln Asp Lys Ser Arg Gly Trp Trp Val His Ser
        115                 120                 125 gtt ctc ttg ctc gag gcc acc aca ttc cgc acc gta gga tta ctg cat     432
Val Leu Leu Leu Glu Ala Thr Thr Phe Arg Thr Val Gly Leu Leu His
    130                 135                 140
```

| | |
|---|---|
| cag gag tgg tgg atg cgc ccg gat gac cct gcc gat gcg gat gaa aag<br>Gln Glu Trp Trp Met Arg Pro Asp Asp Pro Ala Asp Ala Asp Glu Lys<br>145                       150                   155                   160 | 480 |
| gag agt ggc aaa tgg ctg gca gcg gcc gca act agc cgg tta cgc atg<br>Glu Ser Gly Lys Trp Leu Ala Ala Ala Thr Ser Arg Leu Arg Met<br>                      165                   170                   175 | 528 |
| ggc agc atg atg agc aac gtg att gcg gtc tgt gac cgc gaa gcc gat<br>Gly Ser Met Met Ser Asn Val Ile Ala Val Cys Asp Arg Glu Ala Asp<br>         180                   185                   190 | 576 |
| att cat gct tat ctg cag gac aaa ctg gcg cat aac gag cgc ttc gtg<br>Ile His Ala Tyr Leu Gln Asp Lys Leu Ala His Asn Glu Arg Phe Val<br>               195                   200                   205 | 624 |
| gtg cgc tcc aag cac cca cgc aag gac gta gag tct ggg ttg tat ctg<br>Val Arg Ser Lys His Pro Arg Lys Asp Val Glu Ser Gly Leu Tyr Leu<br>210                       215                   220 | 672 |
| tac gac cat ctg aag aac caa ccg gag ttg ggt ggc tat cag atc agc<br>Tyr Asp His Leu Lys Asn Gln Pro Glu Leu Gly Gly Tyr Gln Ile Ser<br>225                       230                   235                   240 | 720 |
| att ccg caa aag ggc gtg gtg gat aaa cgc ggt aaa cgt aaa aat cga<br>Ile Pro Gln Lys Gly Val Val Asp Lys Arg Gly Lys Arg Lys Asn Arg<br>                      245                   250                   255 | 768 |
| cca gcc cgc aag gcg agc ttg agc ctg cgc agt ggg cgc atc acg cta<br>Pro Ala Arg Lys Ala Ser Leu Ser Leu Arg Ser Gly Arg Ile Thr Leu<br>         260                   265                   270 | 816 |
| aaa cag ggg aat atc acg ctc aac gcg gtg ctg gcc gag gag att aac<br>Lys Gln Gly Asn Ile Thr Leu Asn Ala Val Leu Ala Glu Glu Ile Asn<br>               275                   280                   285 | 864 |
| ccg ccc aag ggt gag acc ccg ttg aaa tgg ttg ttg ctg acc agc gaa<br>Pro Pro Lys Gly Glu Thr Pro Leu Lys Trp Leu Leu Leu Thr Ser Glu<br>290                       295                   300 | 912 |
| ccg gtc gag tcg cta gcc caa gcc ttg cgc gtc atc gac att tat acc<br>Pro Val Glu Ser Leu Ala Gln Ala Leu Arg Val Ile Asp Ile Tyr Thr<br>305                       310                   315                   320 | 960 |
| cat cgc tgg cgg atc gag gag ttc cat aag gca tgg aaa acc gga gca<br>His Arg Trp Arg Ile Glu Glu Phe His Lys Ala Trp Lys Thr Gly Ala<br>                      325                   330                   335 | 1008 |
| gga gcc gag agg caa cgc atg gag gag ccg gat aat ctg gag cgg atg<br>Gly Ala Glu Arg Gln Arg Met Glu Glu Pro Asp Asn Leu Glu Arg Met<br>         340                   345                   350 | 1056 |
| gtc tcg atc ctc tcg ttt gtt gcg gtc agg ctg tta cag ctc aga gaa<br>Val Ser Ile Leu Ser Phe Val Ala Val Arg Leu Leu Gln Leu Arg Glu<br>               355                   360                   365 | 1104 |
| agc ttc acg ctg ccg caa gca ctc agg gcg caa ggg ctg cta aag gaa<br>Ser Phe Thr Leu Pro Gln Ala Leu Arg Ala Gln Gly Leu Leu Lys Glu<br>370                       375                   380 | 1152 |
| gcg gaa cac gta gaa agc cag tcc gca gaa acg gtg ctg acc ccg gat<br>Ala Glu His Val Glu Ser Gln Ser Ala Glu Thr Val Leu Thr Pro Asp<br>385                       390                   395                   400 | 1200 |
| gaa tgt cag cta ctg ggc tat ctg gac aag gga aaa cgc aag cgc aaa<br>Glu Cys Gln Leu Leu Gly Tyr Leu Asp Lys Gly Lys Arg Lys Arg Lys<br>                      405                   410                   415 | 1248 |
| gag aaa gca ggt agc ttg cag tgg gct tac atg gcg ata gct aga ctg<br>Glu Lys Ala Gly Ser Leu Gln Trp Ala Tyr Met Ala Ile Ala Arg Leu<br>         420                   425                   430 | 1296 |
| ggc ggt ttt atg gac agc aag cga acc gga att gcc agc tgg ggc gcc<br>Gly Gly Phe Met Asp Ser Lys Arg Thr Gly Ile Ala Ser Trp Gly Ala<br>               435                   440                   445 | 1344 |

```
ctc tgg gaa ggt tgg gaa gcc ctg caa agt aaa ctg gat ggc ttt ctt         1392
Leu Trp Glu Gly Trp Glu Ala Leu Gln Ser Lys Leu Asp Gly Phe Leu
    450                 455                 460 gcc gcc aag gat ctg atg gcg cag ggg atc aag atc tga                     1431
Ala Ala Lys Asp Leu Met Ala Gln Gly Ile Lys Ile
465                 470                 475

<210> SEQ ID NO 2
<211> LENGTH: 476
<212> TYPE: PRT
<213> ORGANISM: Transposon Tn5

<400> SEQUENCE: 2

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
                20                  25                  30

Asn Val Ala Ala Gln Leu Ala Lys Tyr Ser Gly Lys Ser Ile Thr Ile
            35                  40                  45

Ser Ser Glu Gly Ser Glu Ala Met Gln Glu Gly Ala Tyr Arg Phe Ile
    50                  55                  60

Arg Asn Pro Asn Val Ser Ala Glu Ala Ile Arg Lys Ala Gly Ala Met
65                  70                  75                  80

Gln Thr Val Lys Leu Ala Gln Glu Phe Pro Glu Leu Leu Ala Ile Glu
                85                  90                  95

Asp Thr Thr Ser Leu Ser Tyr Arg His Gln Val Ala Glu Glu Leu Gly
            100                 105                 110

Lys Leu Gly Ser Ile Gln Asp Lys Ser Arg Gly Trp Trp Val His Ser
    115                 120                 125

Val Leu Leu Leu Glu Ala Thr Thr Phe Arg Thr Val Gly Leu Leu His
130                 135                 140

Gln Glu Trp Trp Met Arg Pro Asp Asp Pro Ala Asp Ala Asp Glu Lys
145                 150                 155                 160

Glu Ser Gly Lys Trp Leu Ala Ala Ala Thr Ser Arg Leu Arg Met
                165                 170                 175

Gly Ser Met Met Ser Asn Val Ile Ala Val Cys Asp Arg Glu Ala Asp
            180                 185                 190

Ile His Ala Tyr Leu Gln Asp Lys Leu Ala His Asn Glu Arg Phe Val
    195                 200                 205

Val Arg Ser Lys His Pro Arg Lys Asp Val Glu Ser Gly Leu Tyr Leu
210                 215                 220

Tyr Asp His Leu Lys Asn Gln Pro Glu Leu Gly Gly Tyr Gln Ile Ser
225                 230                 235                 240

Ile Pro Gln Lys Gly Val Val Asp Lys Arg Gly Lys Arg Lys Asn Arg
                245                 250                 255

Pro Ala Arg Lys Ala Ser Leu Ser Leu Arg Ser Gly Arg Ile Thr Leu
            260                 265                 270

Lys Gln Gly Asn Ile Thr Leu Asn Ala Val Leu Ala Glu Glu Ile Asn
    275                 280                 285

Pro Pro Lys Gly Glu Thr Pro Leu Lys Trp Leu Leu Leu Thr Ser Glu
290                 295                 300

Pro Val Glu Ser Leu Ala Gln Ala Leu Arg Val Ile Asp Ile Tyr Thr
305                 310                 315                 320

His Arg Trp Arg Ile Glu Glu Phe His Lys Ala Trp Lys Thr Gly Ala
                325                 330                 335
```

```
Gly Ala Glu Arg Gln Arg Met Glu Glu Pro Asp Asn Leu Glu Arg Met
            340                 345                 350

Val Ser Ile Leu Ser Phe Val Ala Val Arg Leu Leu Gln Leu Arg Glu
            355                 360                 365

Ser Phe Thr Leu Pro Gln Ala Leu Arg Ala Gln Gly Leu Leu Lys Glu
            370                 375                 380

Ala Glu His Val Glu Ser Gln Ser Ala Glu Thr Val Leu Thr Pro Asp
385                 390                 395                 400

Glu Cys Gln Leu Leu Gly Tyr Leu Asp Lys Gly Lys Arg Lys Arg Lys
                405                 410                 415

Glu Lys Ala Gly Ser Leu Gln Trp Ala Tyr Met Ala Ile Ala Arg Leu
            420                 425                 430

Gly Gly Phe Met Asp Ser Lys Arg Thr Gly Ile Ala Ser Trp Gly Ala
            435                 440                 445

Leu Trp Glu Gly Trp Glu Ala Leu Gln Ser Lys Leu Asp Gly Phe Leu
            450                 455                 460

Ala Ala Lys Asp Leu Met Ala Gln Gly Ile Lys Ile
465                 470                 475

<210> SEQ ID NO 3
<211> LENGTH: 19
<212> TYPE: DNA
<213> ORGANISM: Transposon Tn5

<400> SEQUENCE: 3
ctgactctta tacacaagt                                              19

<210> SEQ ID NO 4
<211> LENGTH: 19
<212> TYPE: DNA
<213> ORGANISM: Transposon Tn5

<400> SEQUENCE: 4
ctgtctcttg atcagatct                                              19

<210> SEQ ID NO 5
<211> LENGTH: 19
<212> TYPE: DNA
<213> ORGANISM: Transposon Tn5

<400> SEQUENCE: 5
ctgtctctta tacacatct                                              19
```